(12) United States Patent
Baumgartner et al.

(10) Patent No.: US 7,478,344 B2
(45) Date of Patent: Jan. 13, 2009

(54) METHOD AND SYSTEM FOR ENHANCED VERIFICATION BY CLOSELY COUPLING A STRUCTURAL SATISFIABILITY SOLVER AND REWRITING ALGORITHMS

(75) Inventors: Jason R. Baumgartner, Austin, TX (US); Robert L. Kanzelman, Rochester, MN (US); Hari Mony, Austin, TX (US); Viresh Paruthi, Austin, TX (US)

(73) Assignee: International Business Machines Corporation, Armonk, NY (US)

( * ) Notice: Subject to any disclaimer, the term of this patent is extended or adjusted under 35 U.S.C. 154(b) by 400 days.

(21) Appl. No.: 11/443,906

(22) Filed: May 31, 2006

(65) Prior Publication Data

US 2006/0236274 A1      Oct. 19, 2006

(51) Int. Cl.
*G06F 17/50* (2006.01)
(52) U.S. Cl. .................. 716/1; 716/2; 716/6; 716/18
(58) Field of Classification Search .................. 716/1, 716/2, 6, 18
See application file for complete search history.

(56) References Cited

U.S. PATENT DOCUMENTS 6,539,536 B1 *  3/2003  Singh et al. .................. 716/18

* cited by examiner

*Primary Examiner*—Thuan Do
(74) *Attorney, Agent, or Firm*—Casimer K. Salys; Dillon & Yudell LLP (57) ABSTRACT

A method, system and computer program product are disclosed. The method includes initializing a first variable to limit a rewrite time for rewrite operations with respect to an initial design by a rewriting module, a second variable to limit a time for satsifability solver operations with respect to said initial design by a staisfiability solver module and a third variable to limit a maximum number of rewrite iterations with respect to said initial design. A timer is called to track said rewrite time and a local logic rewriting operation is run on said initial design with said rewrite module. In response to determining that all of all targets for said initial design netlist are not solved, whether a rewrite time is expired is determined. In response to determining that said rewrite time is not expired, AND refactoring is run. In response to determining that said rewrite time is not expired, XOR refactoring is run.

1 Claim, 3 Drawing Sheets

METHOD AND SYSTEM FOR ENHANCED VERIFICATION BY CLOSELY COUPLING A STRUCTURAL SATISFIABILITY SOLVER AND REWRITING ALGORITHMS

BACKGROUND OF THE INVENTION

The present application is related to the following co-pending U.S. patent applications, incorporated herein by reference in their entirety:

Ser. No. 11/086,721, filed Mar. 22, 2005 and entitled "METHOD AND SYSTEM FOR REDUCTION OF AND/OR SUBEXPRESSIONS IN STRUCTURAL DESIGN REPRESENTATIONS".

Ser. No. 11/086,720, filed Mar. 22, 2005 and entitled "METHOD AND SYSTEM FOR REDUCTION OF XOR/XNOR SUBEXPRESSIONS IN STRUCTURAL DESIGN REPRESENTATIONS".

1. Technical Field

The present invention relates in general to verifying designs and in particular to reducing resource consumption during verification. Still more particularly, the present invention relates to a system, method and computer program product for performing verification by closely coupling rewriting algorithms and a structural satisfiability solver.

2. Description of the Related Art

With the increasing penetration of processor-based systems into every facet of human activity, demands have increased on the processor and application-specific integrated circuit (ASIC) development and production community to produce systems that are free from design flaws. Circuit products, including microprocessors, digital signal and other special-purpose processors, and ASICs, have become involved in the performance of a vast array of critical functions, and the involvement of microprocessors in the important tasks of daily life has heightened the expectation of error-free and flaw-free design. Whether the impact of errors in design would be measured in human lives or in mere dollars and cents, consumers of circuit products have lost tolerance for results polluted by design errors. Consumers will not tolerate, by way of example, miscalculations on the floor of the stock exchange, in the medical devices that support human life, or in the computers that control their automobiles. All of these activities represent areas where the need for reliable circuit results has risen to a mission-critical concern.

In response to the increasing need for reliable, error-free designs, the processor and ASIC design and development community has developed rigorous, if incredibly expensive, methods for testing and verification for demonstrating the correctness of a design. The task of hardware verification has become one of the most important and time-consuming aspects of the design process.

Among the available verification techniques, formal and semiformal verification techniques are powerful tools for the construction of correct logic designs. Formal and semiformal verification techniques offer the opportunity to expose some of the probabilistically uncommon scenarios that may result in a functional design failure, and frequently offer the opportunity to prove that the design is correct (i.e., that no failing scenario exists).

Unfortunately, the resources needed for formal verification, or any verification, of designs are proportional to design size. Formal verification techniques require computational resources which are exponential with respect to the design under test. Simulation scales polynomially and emulators are gated in their capacity by design size and maximum logic depth. Semi-formal verification techniques leverage formal algorithms on larger designs by applying them only in a resource-bounded manner, though at the expense of incomplete verification coverage. Generally, coverage decreases as design size increases.

Many tasks in computer-aided design (CAD), such as equivalence checking, property checking, logic synthesis, timing analysis, and false-path analysis, require Boolean reasoning on problems derived from circuit structures. The two main approaches used for such applications are Binary Decision Diagrams (BDDs) and Satisfiability (SAT) solving. The former converts the problem into a functionally canonical form, while the latter systematically searches for a consistent assignment of values for the variables of the problem. Typically, SAT solvers are based on the Davis-Putnam procedure that attempts to find a consistent assignment using a branch-and-bound approach. Unsatisfiability is proven if the SAT solver exhaustively enumerates all possible cases without finding a satisfying assignment.

As described in U.S. Pat. No. 6,473,884 B1 (Method and System for Equivalence-Checking Combinational Circuits Using Iterative Binary-Decision-Diagram Sweeping and Structural Satisfiability Analysis), which is incorporated herein by reference in its entirety, BDD sweeping and structural SAT algorithms are applied in an interleaved manner on a shared graph representation of the circuit. Such an intertwined application of these techniques results in a powerful summation of their orthogonal strengths. BDDs work very well if the redundancy of the problem structure eludes an exponential growth during construction. Structural SAT is efficient if the underlying circuit structure can be exploited for effective local search heuristics. In a synergistic setting, an interleaved application of BDD sweeping incrementally reduces the search space for the SAT solver until the problem is solved. The referenced patent focuses on equivalence checking, but this technique can be easily extended to other applications requiring Boolean reasoning such as property checking and false paths analysis.

Unfortunately, prior art systems for multi-algorithmic SAT solving lack the ability to closely integrate the use of closely-integrated rewriting tools to further compact the netlist in an attempt to reduce the search space for the SAT-solver in dimensions qualitatively beyond those possible by mere BDD sweeping, or more generally redundancy removal, alone.

SUMMARY OF THE INVENTION

A method, system and computer program product are disclosed. The method includes initializing a first variable to limit a rewrite time for rewrite operations with respect to an initial design by a rewriting module, a second variable to limit a time for satsifability solver operations with respect to said initial design by a staisfiability solver module and a third variable to limit a maximum number of rewrite iterations with respect to said initial design. A timer is called to track said rewrite time and a local logic rewriting operation is run on said initial design with said rewrite module. In response to determining that all of all targets for said initial design netlist are not solved, whether a rewrite time is expired is determined. In response to determining that said rewrite time is not expired, AND refactoring is run. In response to determining that said rewrite time is not expired, XOR refactoring is run.

BRIEF DESCRIPTION OF THE DRAWINGS

The novel features believed characteristic of the invention are set forth in the appended claims. The invention itself, however, as well as a preferred mode of use, further objects and advantages thereof, will best be understood by reference to the following detailed descriptions of an illustrative embodiment when read in conjunction with the accompanying drawings, wherein:

DETAILED DESCRIPTION OF THE PREFERRED EMBODIMENT

The present invention provides a method, system and computer program product for enhanced verification by closely coupling a satisfiability solver to a rewriting module. The present invention provides a significant advancement over prior art multi-algorithmic SAT solving. In particular, the present invention includes the use of a rich variety of structural rewriting algorithms to further compact a netlist in an attempt to reduce the search space for a closely-coupled SAT-solver in dimensions qualitatively beyond those possible by mere BDD sweeping, or more generally redundancy removal, alone. The rewriting module of the present invention re-forms the logic of a netlist, so as to more optimally represent the function (using fewer logic gates), and eliminates redundancy through techniques such as common subexpression elimination, which is more general than mere redundant-gate elimination, resulting in a greater overall reduction in the netlist size. The use of the rewriting module enables the SAT-solver to discharge the Boolean reasoning problem represented by a given netlist much quicker than possible with prior art.

In the present invention, rewriting algorithms within the rewriting are called in a resource-constrained manner such that the overall approach does not spend excessive time in one particular technique, and the benefits of applying an algorithm, be it rewriting or SAT, are immediately realized by the next algorithm. Such a novel method for tightly and synergistically coupling a structural rewriting and SAT-solving in an interleaved manner results in drastic savings in computational resources for the verification process, enabling design flaws to be exposed and proofs to be completed that otherwise would be infeasible within the specified resources (time and memory).

Figure 1:
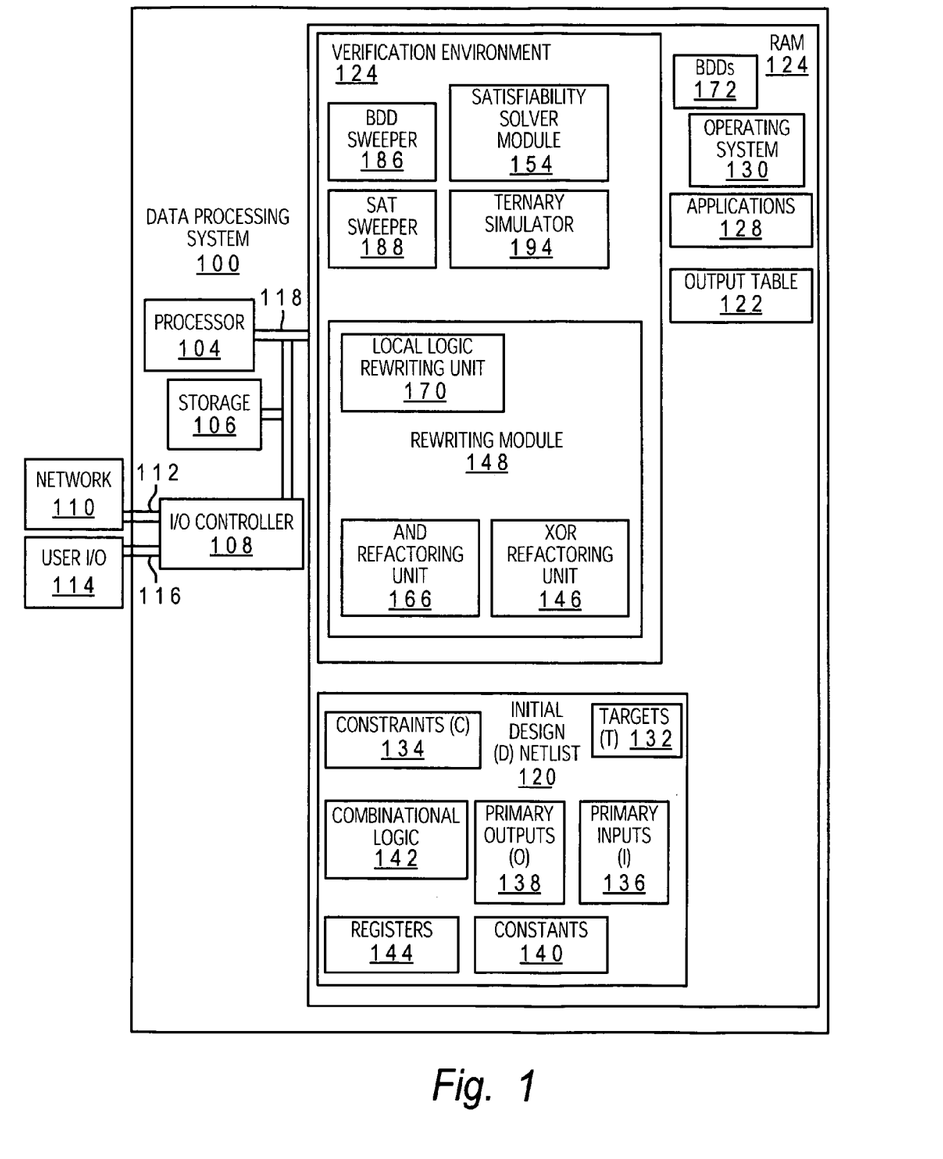
FIG. 1 depicts a block diagram of a general-purpose data processing system with which the present invention of a method, system and computer program product for performing verification by closely coupling rewriting algorithms and a structural satisfiability solver may be performed.

With reference now to the figures, and in particular with reference to FIG. 1, a block diagram of a general-purpose data processing system, in accordance with a preferred embodiment of the present invention, is depicted. Data processing system 100 contains a processing storage unit (e.g., RAM 102) and a processor 104. Data processing system 100 also includes non-volatile storage 106 such as a hard disk drive or other direct-access storage device. An Input/Output (I/O) controller 108 provides connectivity to a network 110 through a wired or wireless link, such as a network cable 112. I/O controller 108 also connects to user I/O devices 114 such as a keyboard, a display device, a mouse, or a printer through wired or wireless link 116, such as cables or a radio-frequency connection. System interconnect 118 connects processor 104, RAM 102, storage 106, and I/O controller 108.

Within RAM 102, data processing system 100 stores several items of data and instructions while operating in accordance with a preferred embodiment of the present invention. These include an initial design (D) netlist 120 and an output table 122 for interaction with a verification environment 124.

In the embodiment shown in FIG. 1, initial design (D) netlist 120 contains targets (T) 132, constants 140, combinational logic 142, registers 144, primary inputs (I) 136, primary outputs (O) 138 and constraints (C) 134. Other applications 128 and verification environment 124 interface with processor 104, RAM 102, I/O control 108, and storage 106 through operating system 130. One skilled in the data processing arts will quickly realize that additional components of data processing system 100 may be added to or substituted for those shown without departing from the scope of the present invention. Other items in RAM 102 include BDDs 172 and modified netlist (D") 166.

Verification environment 124 includes a satisfiability solver module 154, a BDD-sweeper 186, an SAT sweeper 188, a ternary simulator 194, and a rewriting module 148. Rewriting module 148 contains a local logic rewriting unit 170, an AND-refactoring unit 166 and a.

A netlist graph, such as initial design (D) netlist 120, is a popular means of compactly representing problems derived from circuit structures in computer-aided design of digital circuits. Such a representation is non-canonical and offers the ability to analyze the function of circuits from the nodes in initial design (D) netlist 120. Initial design (D) netlist 120 contains a directed graph with vertices representing gates, and edges representing interconnections between those gates. The gates have associated functions, such as constants 140, primary inputs (I) 136 (hereafter also referred to as RANDOM gates), combinational logic 142 such as AND gates, and sequential elements (hereafter referred to as registers 144).

In a preferred embodiment, the method of the present invention is applied to a representation of initial design (D) netlist 120 in which the only combinational gate type within combinational logic 142 is a 2-input AND, and inverters are represented implicitly as edge attributes. Registers 144 have two associated components: their next-state functions, and their initial-value functions. Both are represented as other gates in the graph of initial design (D) netlist 120. Semantically, for a given register 144, the value appearing at its initial-value gate at time, '0' ("initialization" or "reset" time) will be applied as the value of the register 144 itself, while the value appearing at its next-state function gate at time "i" will be applied to the register itself at time "i+1". Certain gates are labeled as targets (T) 132 and constraints (C) 134.

Targets (T) 132 represent nodes whose Boolean expressions are of interest and need to be computed. The goal of the verification process is to find a way to drive a '1' to a target (T) 132 node, or to prove that no such assertion of the target (T) 132 is possible. In the former case, a counterexample trace 190, which shows the sequence of assignments to the inputs in every cycle leading up to the fail event, is generated and recorded to output table 122. Constraints (C) 134 are used to "artificially" limit the stimulus that can be applied to the primary inputs (I) 136 (RANDOM gates) of initial design (D) netlist 120. For instance, a constraint (C) 134 could state that, when searching for a path to drive a '1' to a target (T) 132, verification environment 124 must adhere to the rule that "every constraint (C) 134 gate must evaluate to a logical 1 for every time-step up to, and including, the time-step at which the target is asserted". In such a case, valuations of primary inputs (I) 136 for which the constraint (C) 134 gate evaluates to a '0' are considered invalid.

The directed graph of initial design (D) netlist 120 imposes a topological order amongst the nodes representing any combinational logic of initial design (D) netlist 120. This topological ordering is necessary to avoid the creation of cycles in initial design (D) netlist 120, the creation of which would be semantically unsound. For example, in a 2-input AND/INVERTER representation, verification environment 124 imposes a rule of ordering that the node index of any node is greater than the indices of any of its children. Hence, variables typically tend to assume lower indices compared to AND gates in any combinational logic block within initial design (D) netlist 120. This tendency also implies that, if the variable of initial design (D) netlist 120 under scrutiny is to be composed with a logic cone of initial design (D) netlist 120, e.g., when constraining the values that the variable of initial design (D) netlist 120 can assume by replacing the variable of initial design (D) netlist 120 with a piece of logic that produces the constrained values, a large portion of the nodes in the recursive combinational fanout of the variable within initial design (D) netlist 120 will likely need to be recreated to maintain the topological ordering.

The present invention closely intertwines structural rewriting techniques used by rewriting module 148, structural redundancy removal techniques (BDD-sweeping by BDD sweeper 186 and SAT-sweeping by SAT sweeper 188), and a structural SAT-solver 154. The synergistic union of these techniques offers reductions in problem size, which go qualitatively beyond those possible with prior art and in turn generate exponential speed increases over the prior art.

The structural rewriting techniques used by rewriting module 148 simplify initial design (D) netlist 120 by reforming the logic of initial design (D) netlist 120, so as to enable significant overall reductions in the size of initial design (D) netlist 120. Many such techniques exist and are well-understood by those skilled in the art. BDD-sweeping is a technique to detect structural redundancy in a structural representation of a design by building BDDs 172 within specified size limits, and taking advantage of the canonicity of BDDs 172 to identify gates that have the same logic function, then subsequently merging them. SAT-sweeping uses a combination of simulation by verification environment 124 and SAT-solving by satisfiability solver module 154 to identify redundant gates in initial design (D) netlist 120. Simulation is used by verification environment 124 to identify candidate gates for functional equivalence, followed by application of satisfiability solver module 154 to establish this fact conclusively.

Again, identified redundant gates are merged thus reducing the size of initial design (D) netlist 120. These varied techniques are interleaved with a call to satisfiability solver module 154, which attempts to discharge the Boolean reasoning problem regardless of whether all redundant gates have been identified and merged. The interleaving is controlled by verification environment 124 through the use of resource bounds, such as time and memory resources spent in each of the algorithms, preventing excessive resources from being expended in one algorithm when another algorithm could easily solve the problem, and better enabling a synergistic leveraging of the individual algorithms towards an optimal solution.

Satisfiability solver module 154 operates directly on an AND/INVERTER netlist representation in modified netlist (D") 166, allowing a tight integration of BDD-sweeping and simulation. Satisfiability solver module 154 implements a Davis-Putnam procedure, which, when implemented on modified netlist (D") 166, attempts to find a consistent set of value assignments for the vertices of modified netlist (D") 166 such that the target (T) 132 vertices evaluate to a set of 1s. Satisfiability solver module 154 includes three main steps: Imply, Decide, and Backtrack. The "Imply" step executed by satisfiability solver module 154 propagates all implications based on the current variable assignments within modified netlist (D") 166. For example, a logical '1' at the output of an AND gate in modified netlist (D") 166 implies that all its inputs within modified netlist (D") 166 must also assume a logical '1' value, and a logical '0' at any input of an AND gate implies that the output within modified netlist (D") 166 must also assume a logical '0' value. Once all implications by satisfiability solver module 154 have been made within modified netlist 166, satisfiability solver module 154 performs a "Decide" step, in which satisfiability solver module 154 selects a variable within modified netlist (D") 166, which not yet assigned, and assigns a value (logical '0' or logical '1') to it. The assignment within modified netlist (D") 166 is made and the "Imply" step is repreated.

Satisfiability solver module 154 process repeats these "Imply" and "Decide" steps until all variables within modified netlist (D") 166 are assigned or a conflict is detected. For example, if all inputs of an AND gate are logical '1' but the output is required to be logical '0', satisfiability solver module 154 must backtrack to 'undo' a previous decision. Satisfiability solver module 154 analyzes the conflict to identify the earliest decision responsible for the conflict (through nonchronological backtracking) and records the condition(s) leading to the conflict in the form of a learned clause within learned clauses 180, which can reduce the number of cases that must be explicitly enumerated by satisfiability solver module 154. This reduction feature greatly improves the performance of verification environment 124. Unsatisfiability is proven by satisfiability solver module 154 if an exhaustive evaluation does not uncover an assignment requiring backtracking. Additionally, satisfiability solver module 154 attempts to simplify modified netlist (D") 166 as it learns certain invariant behaviors of modified netlist (D") 166 during processing. For instance, if satisfiability solver module 154 can determine that two nodes are equivalent, satisfiability solver module 154 will merge them to simplify subsequent analysis.

Turning now to rewriting module 148, the present invention employs several optimization techniques to modify initial design (D) netlist 120, which in a general sense can all be labeled forms of "rewriting", that are interleaved by verification environment 124 with the operations of satisfiability solver module 154. Note that rewriting techniques individually are well known to those skilled in the relevant art, hence not explained in detail. Note also that an arbitrary set of rewriting algorithms may be integrated into rewriting module 148 without departing from the scope of the present invention. The preferred embodiment of the present invention is provided for exemplary and not limiting purposes.

Within logic rewriting module, local logic rewriting unit 170 replaces small regions of logic in initial design (D) netlist 120 with more optimal logic performing the same function. Instead of considering only the immediate inputs of a node for functional hashing (i.e. one level backward), local logic rewriting unit 170 allows the structural analysis by verification environment 124 to be extended to multiple levels in the fanin of a vertex. Thus, the granularity to identify functionally identical nodes is extended by local logic rewriting unit 170 to structures with more inputs. Many local rewriting algorithms have been proposed and are usable within local logic rewriting unit 170. As an example, one such algorithm found to be very effective in local logic rewriting unit 170 is four-input rewriting, which identifies a multi-level region of logic within initial design (D) netlist 120 having at most four inputs and replaces the region with an optimal structure selected from a precomputed library of possible implementations, while attempting to ensure maximal sharing with other logic in the fan-out of the region of logic being rewritten.

AND-refactoring unit 166 AND-refactoring unit 166 identifies certain gates initial design (D) netlist 120 (referred to as "roots") whose functions must be preserved when eliminating common subexpressions within AND/OR trees, which in turn indicate which gates may be replaced by the process of the present invention. AND-refactoring unit 166 identifies AND roots in four steps. First, AND-refactoring unit 166 labels all pre-defined gates whose functions need to be preserved as roots. For example, in a verification setting, targets (T) 132 and constraints (C) 134 may need to be preserved. Similarly, in a synthesis setting, "primary outputs" may need to be preserved. Second, AND-refactoring unit 166 marks the "cone of influence" of the pre-defined gates. The cone-of-influence is identified transitively as the set of gates which source incoming edges to this pre-defined set, including next-state functions and initial-value functions for registers. Third, for any register marked as in the cone-of-influence, AND-refactoring unit 166 labels its next-state function and initial-value function as roots. Finally, for any non-register gate "g" in the cone-of-influence, AND-refactoring unit 166 analyzes all gates that source the incoming edges to "g". If "g" is not an AND gate, AND-refactoring unit 166 tags all such source gates as roots. Otherwise, for each incoming edge, if that edge is tagged as "inverted", AND-refactoring unit 166 marks the corresponding source gate as a root.

AND-refactoring unit 166 executes a heuristically optimal structural algorithm for eliminating common AND/OR subexpressions from the identified roots. For all AND-gate roots tagged, AND-refactoring unit 166 traverses fanin-wise exclusively through AND gates and uninverted edges, queueing up "leaves" of the AND tree as all "edges" at which the traversal stops (where an "edge" correlates to both the source gate and the "inverted" attribute of the edge). These edges will include either inverted edges (sourced by arbitrary gate types), or uninverted edges to non-AND gate types. Any gates traversed "through" which are not marked as roots will effectively be replaced by subexpression elimination process, as explained later.

AND-refactoring unit 166 then builds an intermediate data structure representing the common subexpression data. AND-refactoring unit 166 ignores any gate not marked in the cone of influence identified by AND-refactoring unit 166. For any AND gate marked as a root, AND-refactoring unit 166 translates it as a multi-input gate (of the same function) in the intermediate representation whose inputs are the identified leaves. The resulting netlist will include all AND gate roots, and all gates queued up as literals for those roots, with edges between them. AND-refactoring unit 166 then eliminates subexpressions from the created data structure XOR-refactoring unit 146 executes a method for identifying gates of initial design (D) netlist 120 whose functions must be preserved when eliminating common subexpressions within XOR/XNOR trees (referred to as "roots"), which in turn indicate which gates may be replaced by the process of the present invention. XOR-refactoring unit 146 identifies roots in five steps. First XOR-refactoring unit 146 labels all pre-defined gates whose functions need to be preserved as roots. For example, in a verification setting, targets (T) 132 and constraints (C) 134 may need to be preserved. In a synthesis setting, "primary outputs" may need to be preserved.

Second, XOR-refactoring unit 146 marks the "cone of influence" of the pre-defined gates. The cone-of-influence is identified transitively as the set of gates which source incoming edges to this pre-defined set, including next-state functions and initial-value functions for registers. Third, for any register marked as in the cone-of-influence, XOR-refactoring unit 146 labels its next-state function and initial-value function as roots. Fourth, if initial design (D) netlist 120 does not include a 2-input AND representation, for any non-register gate "g" in the cone-of-influence, XOR-refactoring unit 146 analyzes all gates that source the incoming edges to "g". If "g" is not an XOR or XNOR gate, XOR-refactoring unit 146 tags all such source gates as roots. If initial design (D) netlist 120 does include a 2-input AND representation, for every node in the cone of influence, XOR-refactoring unit 146 uses pattern matching to detect the top AND clause of expressions of the form (NOT(A & NOT B) & NOT(NOT A & B)), which is an XNOR structure, and (NOT(A & B) & NOT(NOT A & NOT B)), which is an XOR structure.

If such a structure is detected, XOR-refactoring unit 146 labels the internal two AND gates as "xor_internals". Finally, for every XOR/XNOR gate, XOR-refactoring unit 146 analyzes its fanout gates. If any of the fanout gates are in the cone-of-influence, but not tagged as xor_internals, XOR-refactoring unit 146 labels them as sinks. As a post-processing step, XOR-refactoring unit 146 clears the xor_internal flag from any node identified XOR/XNOR root.

XOR-refactoring unit 146 executes a heuristically optimal structural algorithm for eliminating common XOR/XNOR subexpressions from roots. XOR-refactoring unit 146 exploits the propositional logic fact that ((A XOR B) XNOR C) is equivalent to ((A XNOR B) XOR C), NOT((A XOR B) XOR C) and ((A XOR NOT B) XOR C). Further XOR-refactoring unit 146 exploits the propositional logic fact that ((A XNOR B) XNOR C) is equivalent to ((A XOR B) XOR C). This allows XOR-refactoring unit 146 to cancel NOTs in pairs, and if any NOT remains, XOR-refactoring unit 146 may apply the NOT to the top of the XOR expression.

If initial design (D) netlist 120 does not include a 2-input AND representation, for all XOR/XNOR-gate roots tagged above, XOR-refactoring unit 146 traverses fanin-wise exclusively through XOR/XNOR gates and inversions.

XOR-refactoring unit 146 maintains an inverted_flag, initialized to false. Any XNOR gate traversed through causes XOR-refactoring unit 146 to toggle the inverted_flag, and any inversion present on an edge "between" XOR and XNOR gates causes XOR-refactoring unit 146 to toggle the inverted_flag. Finally, XOR-refactoring unit 146 queues the UNINVERTED gates sourcing edges at which this traversal stops (i.e., inputs to the terminal XOR/XNOR gates). For each such gate that is inverted, XOR-refactoring unit 146 toggles the inverted_flag.

If initial design (D) netlist 120 does include a 2-input AND representation, for all XOR/XNOR-gate roots tagged above, XOR-refactoring unit 146 traverses fanin-wise exclusively through XOR/XNOR structures using a get_xor_literals function. For XOR/XNOR gate "g", XOR-refactoring unit 146 calls a get_xor_leaves(g, false, literals) function with an empty queue "literals" to get its queue of literals, and its inverted_flag.

Ternary simulator 194 performs 3-valued simulation of initial design (D) netlist 120 by applying X's at the inputs, and simulating until no new gates saturate from non-X value to an X implying a fixed-point has been reached, and then looks for constant and equivalent non-X'ed nodes which are subsequently optimized away. Redundant gate elimination identifies and merges functionally identical gates. One such technique is BDD-sweeping with BDD-sweeper 186, as described in U.S. Pat. No. 6,473,884, which is incorporated herein by reference in its entirety, and which takes advantage of the canonicity of BDDs 172 to discover nodes that have the same function. BDD-sweeper 186 propagates BDDs through the netlist with progressively increasing BDD 172 sizes, interleaved with time-constrained calls to the other solving algorithms by verification environment 124. Another technique is SAT-sweeping by SAT sweeper 188, which uses a combination of random simulation and SAT-solving by satisfiability solver module 154 to identify functionally equivalent gates in initial design (D) netlist 120. The simulation by ternary simulator 194 is used to identify candidate gates for functional equivalence, and satisfiability solver module 154 is used to establish this fact conclusively. Again, identified redundant gates are merged thus reducing the size of initial design (D) netlist 120.

Verification environment 124 relies upon a close coupling of satisfiability solver module 154 and rewriting module 148 in an attempt to intertwine them natively to get maximal synergy between rewriting module 148 and satisfiability solver module 154, resulting in dramatically improved performance. The performance of satisfiability solver module 154 is sensitive to, among other things, the size of and redundancy within initial design (D) netlist 120. Thus any reduction in the size of initial design (D) netlist 120 improves performance substantially. While this sensitivity might suggest to the uninitiated a constant application of reduction algorithms to reduce the size of initial design (D) netlist 120 before subjecting it to satisfiability solver module 154, many times it is the case that satisfiability solver module 154 is able to arrive at a solution to the problem much more quickly, especially for targets (T) 132 that can evaluate to a '1' (i.e., "satisfiable" problems) where the satisfiability solver module 154 may quickly converge upon a solution, than the time spent in performing exhaustive rewrites. Hence, there is a fine balance that dictates how much rewriting to perform with rewriting module 148 before invoking satisfiability solver module 154 to solve the problem. Verification environment 124 controls this balance by alternately calling rewriting module 148 to employ various rewrite algorithms in a time-constrained manner and by imposing time-limits on them, followed by subjecting the problem to satisfiability solver module 154 for a specified period of time. These time-limits are dynamically increased over time to weigh the solving process towards proving that the target (T) 132 is unreachable (i.e. the problem is sufficiently hard such that all of the rewrite algorithms used by rewriting module 148 must ultimately be applied "exhaustively" in order to obtain as much reduction as possible before allowing satisfiability solver module 154 to process initial design (D) netlist 120 with full-blown exponential enumeration.

The following pseudo-code outlines an exemplary embodiment of the present invention:

```
Algorithm SAT-solve {
/* Each of the rewrite algorithms polls a "timer" flag intermittently during their processing of
the netlist and has the ability to stop its operation and return if the flag is set, i.e. the time limit
imposed has expired */
        rewrite_time_limit = REWRITE_TIME_LIMIT;            /* initially specified rewrite time
        limit *1
        sat_time_limit = SAT TIME_LIMIT;                    /* initially specified sat time limit */
        max_rewrite_iteration = MAX_REWRITE_ITERATION;      /* initially specified maximum
number of rewrite iterations */
        do {
            reduction = 0; /* records the reduction obtained - e.g., number of netlist gates and
variables */
            rewrite_time_expired = create_new_timer(rewrite_time_limit); /* creates a timer that
asynchronously sets rewrite_time_expired */
            reduction += run_local_logic_rewriting(rewrite_time_expired); /* perform local logic
rewriting and record the cumulative reduction */
            if(rewrite_time_expired or all_targets_solved( )) break;
            reduction += run_and_refactoring(rewrite_time_expired); /* perform and-refactoring and
record the cumulative reduction */
            if(rewrite_time_expired or all_targets_solved( )) break;
            reduction += run_xor_refactoring(rewrite_time_expired); /* perform xor-refactoring and
record the cumulative reduction */
            if(rewrite_time_expired or all_targets_solved( )) break;
            reduction += run_ternary_simulation(rewrite_time_expired); /* perform ternary-simulation
and record the cumulative reduction */
            if(rewrite_time_expired or all_targets_solved( )) break;
            reduction += run_redundant_gate_elimination(rewrite_time_expired); /* perform bdd-
sweeping/sat-sweeping and record the cumulative reduction*/
            if(rewrite_time_expired or all_targets_solved( )) break;
            sat_time_expired = create_new_timer(sat_time_limit); /* creates a timer for the call to the
sat-solver */
            reduction += sat_solve(sat_time_expired);
            increase_resource_limit(rewrite_timelimit, REWRITE_TIME);
            increase_resource_limit(sat_time_limit, SAT_TIME);
            --max_rewrite_iteration;
        } while (reduction && max_rewrite_iteration);
        if(NOT all_targets_solved( )) sat_solve(NULL); /* Run the SAT-solver until all properties
are solved */ }
```

As outlined in the pseudo-code above, time-limits are imposed by verification environment 124 on the various aspects of the overall algorithmic flow to bound their contributions to overall run-time, and these time limits dynamically change over time. In an alternate embodiment, additional criterion is used to restart any aspect of the verification environment 124, e.g., if the reduction at any point exceeds a certain threshold the rewrite loop may be restarted to take advantage of the reduction to squeeze initial design (D) netlist 120 further before subjecting it to satisfiability solver module 154. Additionally, though the pseudo code shows rewriting module 148 being bounded globally by a single "rewrite_time_expired" metric, in an alternate embodiment each algorithm (or sets of algorithms) used by rewriting module 148 may be bounded by their own metrics. The overall approach of the present invention is that verification environment 124 first attempts to apply the rewrite algorithms of rewriting module 148 in a time-bounded fashion while also applying a low-cost pass by satisfiability solver module 154. If the problem is still unsolved, then the resource limits are increased and the process is repeated, allowing more resources to be spent in the respective phases assuming that the problem is increasingly more difficult. When increasing the resource limit verification environment 124 multiplies the current limit by a constant factor (>1.0). This multiplication continues until no more reductions by rewriting module 148 are obtained, or until an overall limit on the maximum number of iterations allowed through the rewrite loop has occurred, then the problem is subjected to a final call to satisfiability solver module 154. with infinite resources, i.e. until the problem is solved.

The present invention has enabled verification environment 124 to solve many problems otherwise not possible by satisfiability solver module 154 by dynamically adjusting to the difficulty of the problem over time and investing more time in simplifying and reducing the before subjecting it to an exhaustive search by satisfiability solver module 154. Rewriting module 148 and satisfiability solver module 154 operate synergistically by unlocking reduction potential for each other, and dramatically reducing the search space for satisfiability solver module 154.

Note that the ability to integrate rewriting module 148 with a satisfiability solver module 154 algorithm has pervasive improvements, not only for stand-alone satisfiability solver module 154 solution, but also, e.g. for other applications 128 that perform temporal analysis of sequential initial design (D) netlist 120. For example, if the goal is to use algorithms from satisfiability solver module 154 to perform bounded falsification or induction analysis of a initial design (D) netlist 120, one may wish to employ combinational rewriting algorithms from rewriting module 148 to that sequential initial design (D) netlist 120 to reduce its complexity prior to the bounded "unfolded" analysis by a satisfiability solver module 154. Without such rewriting algorithms as are contained within rewriting module 148 satisfiability solver module 154, prior art is unable to achieve nearly the performance achievable with the present invention.

Note again that the reduction algorithms outlined above as part of rewriting module 148 are a representative set of algorithms to explain the overall intertwined application of rewrite algorithms within rewriting module 148 and satisfiability solver module 154, and additional algorithms can easily be integrated in the overall scheme without departing from the scope and intent of the present invention. It may also be noted that the present invention can also be used as a general redundancy removal solution by simply not calling out the terminal satisfiability solver module 154, and the reduced initial design (D) netlist 120 after rewrites and reduction would significantly improve performance of any structural reduction/reasoning/decision/synthesis procedure.

Figures 2, 2A:
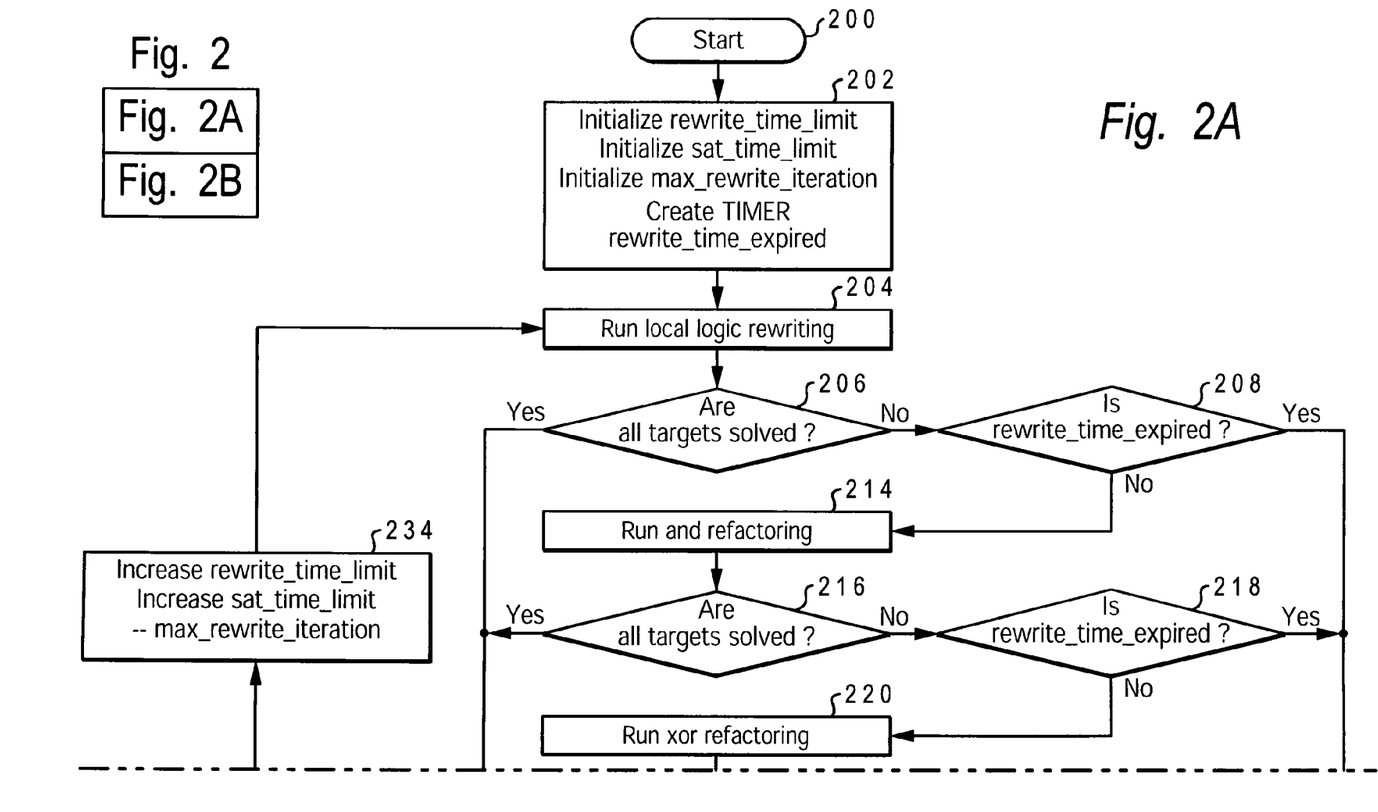
FIG. 2 is a high-level logical flowchart of a process for performing verification by closely coupling rewriting algorithms and a structural satisfiability solver.
Figure 2B:
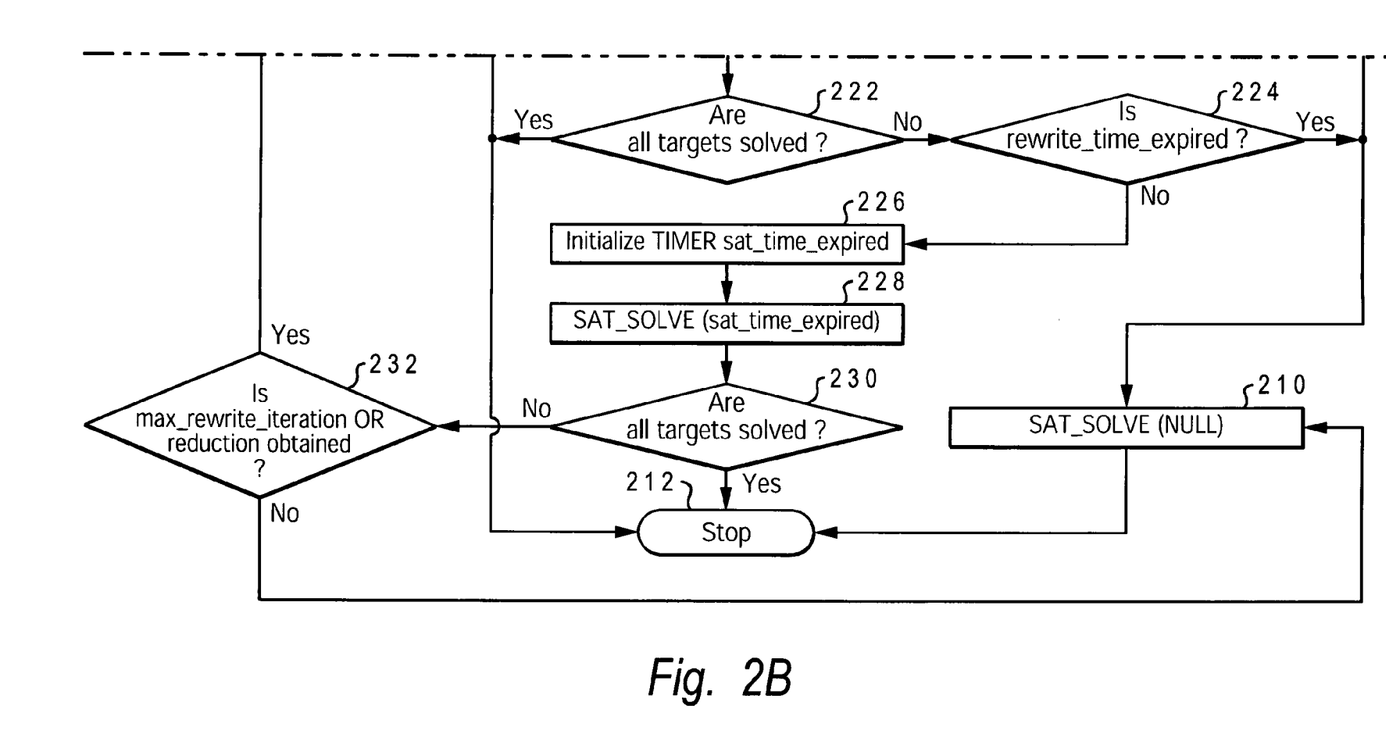

Turning now to FIG. 2, a high-level logical flowchart of a process for performing verification by closely coupling a rewriting module and a structural satisfiability solver is depicted. The process starts at step 200 and then proceeds to step 202, which depicts verification environment 124 initializing several variables and creating a rewrite time expiration counter. The variables initialized at step 204 by verification environment 124 include a time limit for the operations of rewrite module 148, a time limit for the operations of satisfiability solver module 154, and a maximum number of acceptable rewrite iterations. The process next moves to step 204, which illustrates rewriting module 148 performing local logic rewriting with local logic rewriting unit 170. The process then proceeds to step 206, which illustrates verification environment 124 determining whether all targets (T) 132 are solved for initial design (D) netlist 120. If verification environment 124 determines that all targets (T) 132 are solved for initial design (D) netlist 120, then the process ends at step 212. However, if verification environment 124 determines that all targets (T) 132 are not solved for initial design (D) netlist 120, then the process next moves to step 208. Step 208 depicts verification environment 124 determining whether the time limit for the operations of rewrite module 148 is expired.

If verification environment 124 determines that the time limit for the operations of rewrite module 148 is expired, then the process proceeds to step 210, which depicts satisfiability solver module 154 performing a non-time-bounded satisfiability (SAT_SOLVE(NULL)) operation. The process then ends at step 212. Returning to step 208, if verification environment 124 determines that the time limit for the operations of rewrite module 148 is not expired, then the process proceeds to step 214. Step 214 illustrates rewriting module 148 performing AND refactoring with AND refactoring unit 166. The process next moves to step 216, which illustrates verification environment 124 determining whether all targets (T) 132 are solved for initial design (D) netlist 120. If verification environment 124 determines that all targets (T) 132 are solved for initial design (D) netlist 120, then the process ends at step 212. However, if verification environment 124 determines that all targets (T) 132 are not solved for initial design (D) netlist 120, then the process next moves to step 218. Step 218 depicts verification environment 124 determining whether the time limit for the operations of rewrite module 148 is expired.

If verification environment 124 determines that the time limit for the operations of rewrite module 148 is expired, then the process proceeds to step 210, which is described above. Returning to step 218, if verification environment 124 determines that the time limit for the operations of rewrite module 148 is not expired, then the process proceeds to step 220. Step 220 illustrates rewriting module 148 performing XOR refactoring with XOR refactoring unit 146. The process next moves to step 222, which illustrates verification environment 124 determining whether all targets (T) 132 are solved for initial design (D) netlist 120. If verification environment 124 determines that all targets (T) 132 are solved for initial design (D) netlist 120, then the process ends at step 212. However, if verification environment 124 determines that all targets (T) 132 are not solved for initial design (D) netlist 120, then the process next moves to step 224. Step 224 depicts verification environment 124 determining whether the time limit for the operations of rewrite module 148 is expired.

If verification environment 124 determines that the time limit for the operations of rewrite module 148 is expired, then the process proceeds to step 210, which is described above. Returning to step 218, if verification environment 124 determines that the time limit for the operations of rewrite module 148 is not expired, then the process proceeds to step 226. Step 226 illustrates verification unit 124 initializing a timer for determining when time has expired for the use of satisfiability solver module 154. The process next moves to step 228, which depicts satisfiability solver module 154 performing a time bounded satisfiability (SAT_SOLVE(sat_time_expired)) operation, bounded by the variable sat_time_expired. The process then proceeds to step 230. Step 230 illustrates verification environment 124 determining whether all targets (T) 132 are solved for initial design (D) netlist 120. If verification environment 124 determines that all targets (T) 132 are solved for initial design (D) netlist 120, then the process ends at step 212. However, if verification environment 124 determines that all targets (T) 132 are not solved for initial design (D) netlist 120, then the process next moves to step 232, which depicts verification environment 124 determining whether the maximum number of rewrite iterations has been performed by rewrite module 148 or the maximum amount of possible reduction of initial design (D) netlist 120 has been obtained.

If verification environment 124 determines that the maximum number of rewrite iterations has been performed by rewrite module 148 or the maximum amount of possible reduction of initial design (D) netlist 120 has not been obtained, then the process returns to step 210, which is described above. If, however, verification environment 124 determines that the maximum number of rewrite iterations has been performed by rewrite module 148 or the maximum amount of possible reduction of initial design (D) netlist 120 has been obtained, then the process next moves to step 234, which depicts verification environment 124 increasing several variables. The variables increased at step 204 by verification environment 124 include a time limit for the operations of rewrite module 148, a time limit for the operations of satisfiability solver module 154, and a maximum number of acceptable rewrite iterations. The process next returns to step 204.

While the invention has been particularly shown as described with reference to a preferred embodiment, it will be understood by those skilled in the art that various changes in form and detail may be made therein without departing from the spirit and scope of the invention. It is also important to note that although the present invention has been described in the context of a fully functional computer system, those skilled in the art will appreciate that the mechanisms of the present invention are capable of being distributed as a program product in a variety of forms, and that the present invention applies equally regardless of the particular type of signal bearing media utilized to actually carry out the distribution. Examples of signal bearing media include, without limitation, recordable type media such as floppy disks or CD ROMs and transmission type media such as analog or digital communication links.

What is claimed is:

1. A method in a data processing system, said method comprising:

initializing a first variable to limit a rewrite time for rewrite operations with respect to an initial design by a rewriting module;

initializing a second variable to limit a time for satisfiability solver operations with respect to said initial design by a satisfiability solver module;

initializing a third variable to limit a maximum number of rewrite iterations with respect to said initial design;

increasing said first variable to limit said rewrite time for rewrite operations by said rewriting module, increasing said second variable and subsequently performing a non-time bounded satisfiability analysis;

calling a timer to track said rewrite time;

running a local logic rewriting operation on said initial design with said rewrite module;

in response to determining that all targets for an initial design netlist are not solved, determining whether a rewrite time is expired;

in response to determining that said rewrite time is not expired, running AND refactoring, wherein running said AND refactoring includes:

selecting a first simplification mode for said initial design from a set of applicable simplification modes, wherein said first simplification mode is an AND/OR simplification mode;

performing a simplification of said initial design according to said first simplification mode to generate a reduced design;

determining whether a size of said reduced design is less than a size of said initial design; and in response to determining that said size of said reduced design is less than said size of said initial design, replacing said initial design with said reduced design; and in response to determining that said rewrite time is not expired, running XOR refactoring, wherein performing said XOR refactoring further comprises:

selecting a first simplification mode for said initial design from a set of applicable simplification modes, wherein said first simplification mode is an XOR/XNOR simplification mode;

performing a simplification of said initial design according to said first simplification mode to generate a reduced design containing a reduced number of XOR gates;

determining whether a size of said reduced design is less than a size of said initial design; and in response to determining that said size of said reduced design is less than a said size of said initial design, replacing said initial design with said reduced design;

determining one or more of: (a) whether said all targets for said initial design netlist are solved, (b) whether said rewrite time is expired, and (c) whether said variable to limit a maximum number of rewrite iterations is obtained.

* * * * *